United States Patent [19]

Pemberton

[11] 4,150,436
[45] Apr. 17, 1979

[54] FIRST ORDER SAMPLE AND HOLD

[75] Inventor: Troy J. Pemberton, Bartlesville, Okla.

[73] Assignee: Phillips Petroleum Company, Bartlesville, Okla.

[21] Appl. No.: 864,125

[22] Filed: Dec. 23, 1977

[51] Int. Cl.² ............... G06G 7/30; G01N 31/08
[52] U.S. Cl. ............................. 364/853; 73/23.1
[58] Field of Search ............. 73/23.1; 364/853, 723, 364/602

[56] References Cited

U.S. PATENT DOCUMENTS

| | | | |
|---|---|---|---|
| 2,972,447 | 2/1961 | White | 364/105 |
| 3,057,584 | 10/1962 | Bretoi | 318/561 |
| 3,185,820 | 5/1965 | Williams et al. | 73/23.1 |
| 3,246,130 | 4/1966 | Rubin | 364/723 |
| 3,399,300 | 8/1968 | Silverman | 364/800 |
| 3,527,926 | 9/1970 | Holy | 73/23.1 |
| 3,617,716 | 11/1971 | Schulz | 364/723 |
| 3,714,813 | 2/1973 | Martin | 73/23.1 |
| 4,073,009 | 2/1978 | Andow et al. | 364/602 |

*Primary Examiner*—Stephen A. Kreitman

[57] ABSTRACT

A method and apparatus is provided which can correctly reproduce any signal with a constant slope in time. The signal of interest is sampled at two different times $t_1$ and $t_2$. The two sampled values are then utilized to predict the value of the signal of interest at a time $t_3$. In this manner trend information is provided concerning the signal of interest between the sample times $t_2$ and $t_3$.

4 Claims, 4 Drawing Figures

FIRST ORDER SAMPLE AND HOLD

This invention relates to a method and apparatus for implementing a first order sample and hold.

As used herein the term first order sample and hold refers to a circuit which can correctly reproduce any signal with constant slope in time. The term zero order sample and hold refers to a circuit which can correctly reproduce only a constant, nonvarying signal.

In the past zero order sample and hold circuits have been used to approximate a desired signal of varying slope by sampling the desired signal at intervals and using the sampled values to provide a control signal to a controller or provide information to a recording system as well as other applications. However, inaccuracies arise when the signal being sampled by a zero order sample and hold circuit has a non-zero slope in time. The zero order sample and hold circuit provides no trend information between sample times, i.e. the output signal has the form of a stairstep with each horizontal step having a constant value equal to the respective sampled value. Thus information on changes between sampling times is lost, and a controller will not have the latest information on which to act except at the exact point in time of sampling. When a zero order sample and hold circuit is used a controller must be detuned more than would otherwise be necessary to maintain control loop stability.

A first order sample and hold would solve the problems inherent in a zero order sample and hold by providing trend information between sample periods. Accordingly, it is an object of this invention to provide a method and apparatus for implementing a first order sample and hold.

In accordance with the present invention a method and apparatus is provided whereby the signal of interest which will be referred to as X(t) is sampled at two different points in time to provide values $Y(t_1)$ and $Y(t_2)$. The sampled values $Y(t_1)$ and $Y(t_2)$ are then combined in such a manner as to provide a prediction of the value of the signal X(t) at a time $t_3$. In this manner trend information is provided concerning the signal X(t) between the sample points $t_2$ and $t_3$.

Other objects and advantages of the invention will be apparent from the description of the invention and the appended claims as well as from the detailed description of the drawings in which:

The invention is illustrated and described in terms of a specific embodiment wherein a first order sample and hold circuit is utilized to sample the output signal of a chromatographic analyzer and provide a signal representative of the chromatographic analyzer output signal to a recording means. Although the invention is illustrated and described in terms of the sampling of the output signal of a chromatographic analyzer, the applicability of the invention extends to any application where a sample and hold circuit may be utilized.

Figure 1:
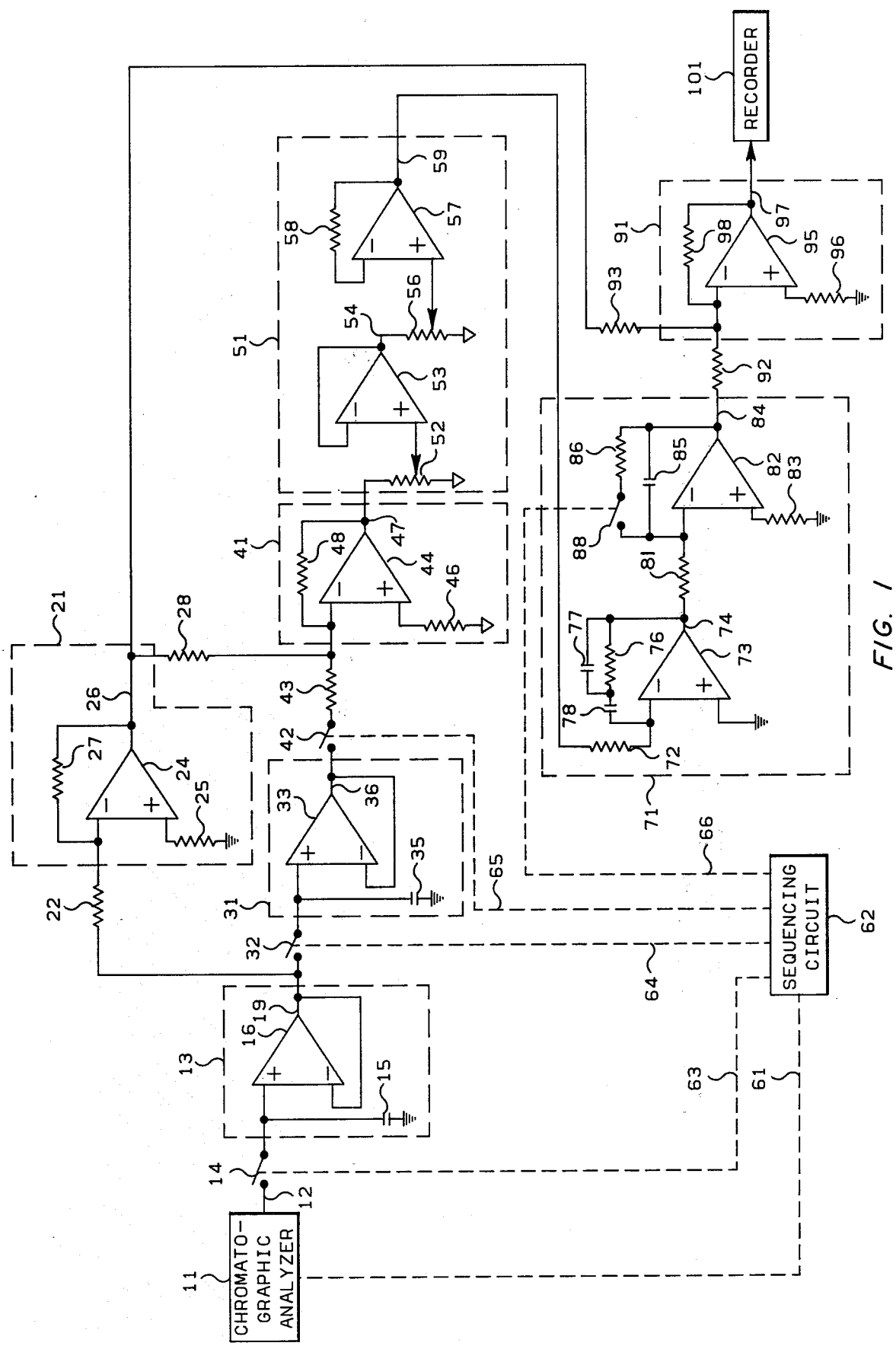
FIG. 1 is a schematic of a first order sample and hold circuit in accordance with the present invention.

Referring to the drawings and in particular to FIG. 1, chromatographic analyzer means 11 outputs a signal 12 representative of a process measurement signal. Signal 12 is supplied as an input to a first zero order sample and hold circuit 13. Signal 12 is supplied directly to the non-inverting terminal of operational amplifier 16 and to one terminal of capacitor 15 when switching means 14 is closed. The other terminal of capacitor 15 is grounded. The output signal 19 from operational amplifier 16 is fed back to the inverting terminal of operational amplifier 16. The output signal 19 from operational amplifier 16 is supplied to an input to the inverting circuit 21. Signal 19 is supplied through resistor 22 to the inverting terminal of operational amplifier 24. The non-inverting terminal of operational amplifier 24 is grounded through resistor 25. The output signal 26 of operational amplifier 24 is fed back to the inverting terminal of operational amplifier 24 through resistor 27. The output signal 26 from operational amplifier 24 is also supplied as an input to a first summing circuit 41 and a second summing circuit 91.

When switching means 32 is closed the output signal 19 from operational amplifier 16 is supplied to a second zero order sample and hold circuit 31. Signal 19 is supplied to the non-inverting terminal of operational amplifier 33 and is also supplied to one terminal capacitor 35, the other terminal of capacitor 35 being grounded. The ouput signal 36 of operational amplifier 33 is fed back to the inverting terminal of operational amplifier 33.

When switching means 42 is closed, the output signal 36 of operational amplifier 33 is supplied as an input to a summing circuit 41. Signal 36 is supplied to the inverting terminal of operational amplifier 44 through resistor 43. Signal 26 is also supplied to the inverting terminal of operational amplifier 44 through resistor 28. The non-inverting terminal of operational amplifier 44 is grounded through resistor 46. The output signal 47 of operational amplifier 44 is fed back to the inverting terminal of operational amplifier 44 through resistor 48. Signal 47 is also supplied as an input to the voltage divider circuit 51. Signal 47 is supplied through potentiometer 52 to the non-inverting input of operational amplifier 53. The output signal 54 from operational amplifier 53 is fed back to the inverting input of operational amplifier 53. Signal 54 is also supplied through potentiometer 56 to the non-inverting input of operational amplifier 57. The output signal 59 from operational amplifier 57 is fed back through resistor 58 to the inverting input of operational amplifier 57. Signal 59 is also supplied as an input to the integrating circuit 71. Signal 59 is supplied to the inverting terminal of operational amplifier 73 through resistor 72. The non-inverting terminal of operational amplifier 73 is grounded. The output signal 74 from operational amplifier 73 is fed back to the inverting terminal of operational amplifier 73 through a resistor capacitance network made up of resistor 76 and capacitors 77 and 78. The output signal 74 from operational amplifier 73 is also supplied to the inverting terminal of operational amplifier 82 through resistor 81. The non-inverting terminal of operational amplifier 82 is grounded through resistor 83. When switching means 88 is open the output signal 84 from operational amplifier 82 is fed back to the inverting terminal of operational amplifier 82 through capacitor 85. When switching means 88 is closed the output signal 84 from operational amplifier 82 is fed back to the inverting terminal of operational amplifier 82 through a resistance capacitor network made up of capacitor 85 and resistor 86. Signal 84 is also supplied as an input signal to a second summing network 91. Signal 84 is supplied through resistor 92 as one input to the inverting terminal of operational amplifier 95. The output signal 26 from operational amplifier 24 is supplied through resistor 93 as a second input to the inverting terminal of operational amplifier 95. The non-inverting terminal of operational amplifier 95 is grounded through resistor 96. The output signal 97 of operational amplifier 95 is fed back to the inverting terminal of operational amplifier 95 through resistor 98. The output signal 97 from operational amplifier 95 is also supplied to a recording means 101 in this preferred embodiment. Signal 97 could be supplied to a control element or any desired source.

Chromatographic analyzer means 11 provides an initiation signal 61 to the sequencing circuit 62 at the beginning of every analyzer cycle. The sequencing circuit 62 provides control signals for the various switching means. Signal 63 is provided as a control signal to switching means 14. Signal 64 is provided as a control signal to switching means 32. Signal 65 is supplied as a control signal to switching means 42. Signal 66 is supplied as a control signal to switching means 88. The sequencing circuit 62 is used to switch the hold function of the zero order sample and hold circuits 13 and 31 and to reset integration in the integrating circuit 71.

As has been stated the circuit shown in FIG. 1 operates functionally as a first order sample and hold circuit. The sequential events necessary to form the desired output signal 97 are controlled by the sequencing circuit 62. The output signals from the sequencing circuit 62 will be equal to logic 1 (high) when it is desired to close the respective switching means associated with each control signal. The switching means are closed in order for a desired period of time as determined by the circuitry of the sequencing circuit 62. Switching means 32 is closed first then switching means 14, 42, and 88 are closed in that order. The switching means are closed only for the period of time that their respective command signal remains high and will open immediately when their respective command signal becomes equal to logic 0 (low). Only one switching means is closed at any one time.

Switching means 32 is closed first but capacitor 35 will not recieve any charge because capacitor 15 has not been charged. Switching means 14 is then closed and capacitor 15 is charged to the voltage level of signal 12. When capacitor 15 is charged then the output signal 19 from operational amplifier 16 will have the same voltage level as signal 12. Signal 26 will also have the same voltage level as signal 12 but signal 26 will be inverted. Signal 12 is representative of the output signal of chromatographic analyzer means 11 at a time t and will be referred to as X(t). Signal 19 is representative of the sampled value of X(t) and will be referred to as $Y(t_1)$. Signal 26 is thus equal to $-Y(t_1)$. Signal 26 is supplied as one input to the summing circuit 41. Switching means 42 is closed and signal 36 is supplied as a second input to summing circuit 41 but signal 36 will have a zero voltage level because capacitor 35 has not been charged. The output signal 47 from operational amplifier 44 will thus be equal to $Y(t_1)$. Signal 47 is supplied as an input to the voltage divider network 51. The voltage divider network is tuned so as to output a signal 59 representative of the input signal 47 divided by the chromatographic analyzers cycle time T. Signal 59 is thus representative of $Y(t_1)/T$. Signal 59 is integrated by the integrating circuit 71 to produce an output signal 84 representative of $-Y(t_1)/T$ t. Signal 84 and signal 26 are summed by the summing network 91 to produce an output signal 97 representative of $Y(t_1)+(Y(t_1)/T)$ t. This output could be achieved by a zero order sample and hold.

The desired first order sample and hold function is achieved on the second cycle. Switching means 88 is closed to reset the integrating circuit 71. Switching means 32 is closed for the second time. This time capacitor 35 will be charged to the voltage level of signal 19. When capacitor 35 is charged, the output signal 36 from operational amplifier 33 will have the same voltage level as signal 19. This voltage level has been referred to as $Y(t_1)$. Switching means 12 is then closed and capacitor 15 is now charged to the voltage level of signal 12 which will now be representative of the output signal of chromatographic analyzer means 11 at a time $t_2$. Signal 19 will again be representative of the sample value of signal 12 at a time $t_2$ and will be referred to as $Y(t_2)$. Likewise, signal 26 will now be equal to $-Y(t_2)$. Signal 26 will again be supplied as one input to the summing circuit 41. Switching means 42 will again be closed but this time signal 36 will have a voltage level equal to the voltage level of capacitor 35 and will be referred to as $Y(t_1)$. The output signal 47 from operational amplifier 44 will thus be equal to $Y(t_2)-Y(t_1)$. Signal 47 is supplied as an input to the voltage divider network 51. As has been stated the voltage divider network will again be tuned so as to output a signal 59 representative of the input signal 47 divided by the chromatographic analyzers cycle time T. Signal 59 is thus representative of $(Y(t_2)-Y(t_1))/T$. Signal 59 is integrated by the integrating circuit 71 to produce an output signal 84 representative of $(-Y(t_2)+Y(t_1))/T$ t. Signal 84 and signal 26 are summed by the summing network 91 to produce an output signal 97 representative of $Y(t_2)+(Y(t_2)-Y(t_1))/T$ t. This is the desired output of a first order sample and hold.

Figure 2:
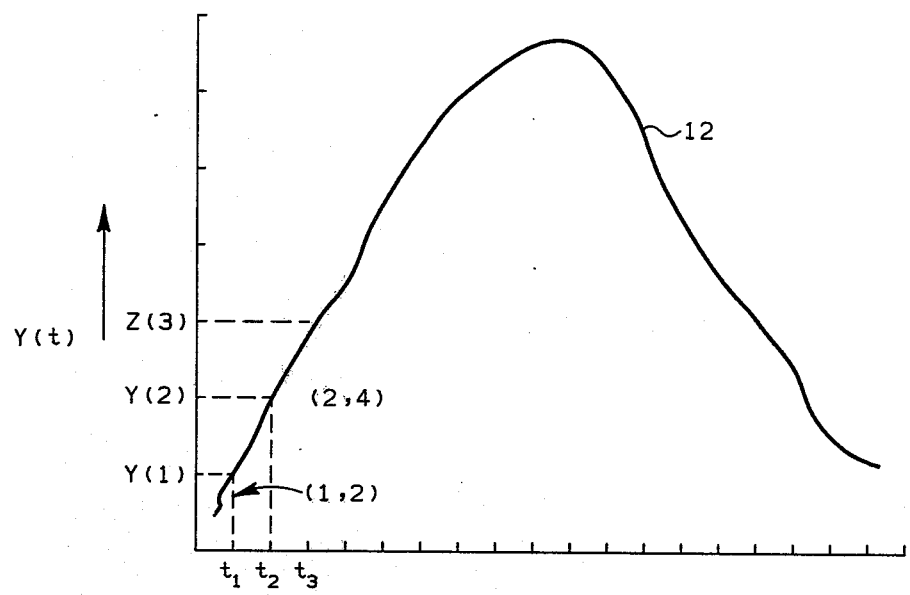
FIG. 2 is an example of the use of the first order sample and hold circuit illustrated in FIG. 1.

A simplified example of the use of the first order sample and hold circuit illustrated in FIG. 1 is presented in FIG. 2. Signal 12 is shown as the typical output of chromatographic analyzer 11 in FIG. 1. Referring back to the terminology used in the description of FIG. 1 and comparing this terminology to FIG. 2 gives the following correlation:

$$Y(t_1) = Y(1) = 2$$

$$Y(t_2) = Y(2) = 4$$

$$T = t_2 - t_1 = 1$$

The output of the first order sample and hold circuit illustrated in FIG. 1 has been shown to be given by the equation $$Z(t) = Y(t_2) + (Y(t_2) - Y(t_1))/T) \, t \qquad (1)$$

where Z(t) represents the output of the first order sample and hold. Using the numbers derived from the example shown in FIG. 2 and solving for Z(t) at a time $t_3$ gives a value of 6 for Z(t) at a time $t_3$. This is a prediction of the value of signal 12 at time $t_3$. As is shown in FIG. 2 the predicted value is very close to the actual value of signal 12 at time $t_3$.

Figure 3:
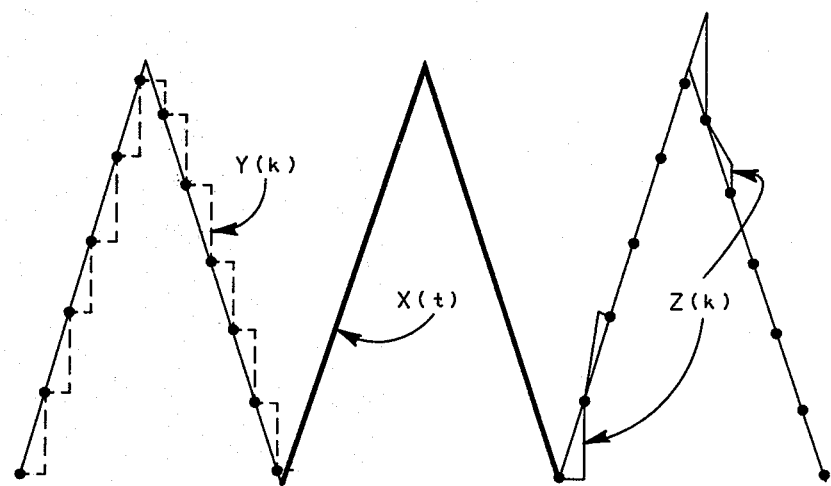
FIG. 3 is a comparison of the outputs of a zero order sample and hold and a first order sample and hold.

The advantages of a first order sample and hold over a zero order sample and hold are illustrated in FIG. 3.

The signal X(t) shown in FIG. 3 is the simulated output of a chromatographic analyzer. A linear output was simulated for ease of illustration. The signal Y(k) is the simulated output of a zero order hold circuit to which the signal X(t) is supplied as an input. The signal Z(k) is the simulated output of a first order sample and hold circuit to which the signal X(t) is supplied as an input.

As can be seen in FIG. 3 the signal Y(k) is held constant for a period of time equal to the chromatographic analyzer cycle time. X(t) is then sampled again and the signal Y(k) assumes a new value. Note that Y(k) does not follow X(t) between sample periods. This results in a loss of information which forces a controller to which the signal Y(k) is being provided to be detuned more than would otherwise be necessary in order to maintain control loop stability.

This problem is solved by a first order sample and hold circuit. As is shown in FIG. 3, the output of a first order sample and hold circuit follows the signal X(t) between sample periods. It took two sample periods to match signal Z(k) to signal X(t) but then the output of the first order sample and hold circuit followed the signal X(t) exactly for three sample periods. When signal X(t) reversed, the signal Z(k) overshot but after one more sample period the output of the first order sample and hold circuit Z(k) was again tracking the signal X(t). In this manner, the first order sample and hold provides information to a controller or recorder between sample periods and prevents any loss of information between sample periods.

If the slope of the curve X(t) were constantly changing rather than a sawtooth function the first order sample and hold circuit would not track the curve exactly but would rather generate a prediction of the value of the next sample point. The prediction would be corrected at each sample time. The prediction would still provide more accurate information to a controller than is possible with a zero order sample and hold circuit.

Figure 4:
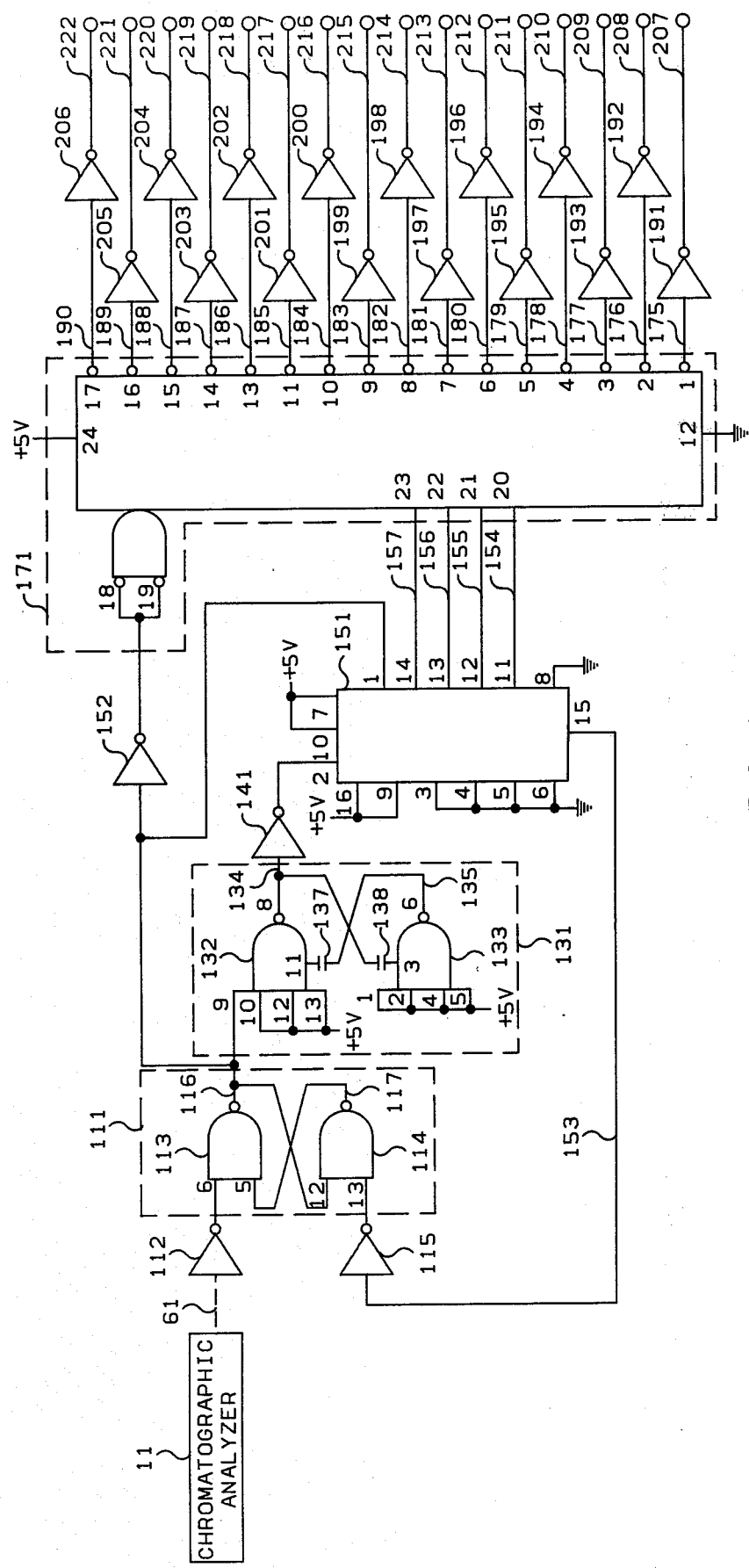
FIG. 4 is a schematic of the sequencing circuit shown in FIG. 1.

FIG. 4 is a schematic of sequencing circuit 62 shown in FIG. 1. Many different types of sequencing circuits are available; FIG. 4 is a preferred embodiment of one such circuit.

The control signal 61 from chromatographic analyzer 11 is supplied to the two input buffer circuit 111 at the beginning of each chromatographic analyzer cycle. Control signal 61 is, in a preferred embodiment, a five volt square wave. Signal 61 is supplied as an input to pin 6 of NAND gate 113 through inverter 112. The output signal 116 of NAND gate 113 is supplied as an input to pin 12 of NAND gate 114. The output signal 117 from NAND gate 114 is supplied as an input to pin 5 of NAND gate 113. The output signal 116 of NAND gate 113 is also supplied as an input to the dual four input buffer circuit 131. Signal 116 is supplied to pin 9 of NAND gate 132. Pins 10, 12 and 13 of NAND gate 132 are tied to a +5 volt power supply. The output signal 134 of NAND gate 132 is supplied as an input to pin 3 of NAND gate 133 through capacitor 138. Pins 1, 2, 4, and 5 of NAND gate 138 are tied to a +5 volt power supply. The output signal 135 of NAND gate 133 is supplied as an input to pin 11 of NAND gate 132 through capacitor 137. The output signal 134 of NAND gate 132 is supplied through inverter 141 to pin 2 of a synchronous four-bit binary counter 151. Pin 7, 9, 10 and 16 of the synchronous four-bit binary counter 151 are tied to a +5 volt power supply. Pins 3, 4, 5, 6 and 8 of the synchronous four-bit binary counter 151 are tied to ground. Signal 153 from pin 15 of the synchronous four-bit binary counter 151 is supplied as an input to pin 13 of NAND gate 114 through inverter 115. The output signal 116 from NAND gate 113 is supplied as an input to pin 1 of the synchronous four-bit binary counter 151. Signals 154–157 from pins 11–14 of the synchronous four-bit binary counter 151 are supplied as inputs to pins 20–23 of a four-line-to-sixteen-line decoder/demultiplexer 171. The output signal 116 from NAND gate 113 is supplied as an input to pins 18 and 19 of the four-line-to-sixteen-line decoder/demultiplexer through inverter 152. Pin 24 of the four-line-to-sixteen-line decoder/demultiplexer is tied to a +5 volt power supply. Pin 12 of the four-line-to-sixteen-line decoder/demultiplexer is tied to ground. The output signals 175–190 from pins 1–11 and 13–17 of the four-line-to-sixteen-line decoder/demultiplexer 171 are inverted by inverters 191–206 to form signals 207–122 which are the output signals from sequencing circuit 62. Sixteen output signals from the sequencing circuit 62 are available. However, only four of the available output signals from the sequencing circuit 62 are used in the preferred embodiment of this invention.

The sequencing circuit shown in FIG. 4 functions as follows. The control signal 61 from the chromatographic analyzer 11 goes high at the beginning of a chromatographic analyzer cycle period. Signal 61 is inverted by inverter 112 to provide a low input to pin 6 of NAND gate 113. When this occurs, the output signal 116 from NAND gate 113 will go high. When the output signal 116 from NAND gate 113 goes high, the dual four-input buffer 131 is enabled and will produce a series of gated pulses of an approximate frequency of $$f = 200/c$$

where f is frequency in MHz and C is the capacitance of capacitor 137 in picofarads. In this preferred embodiment, capacitor 137 has a value of 1 μf thus $$f = 200 \text{ Hz}$$

The pulse will have a duration of time T given by $$T = 0.5 \, C$$

where T is in nanoseconds and C is the capacitance of capacitor 138 in picofarads. In this preferred embodiment capacitor 138 is 0.02 μf and T = 10 μsec. Signal 134 will thus be made up of a series of pulses which will be low. Signal 134 is inverted by inverter 141 to obtain a series of high signals which will clock the synchronous four bit binary counter 151 to make it count to 15.

The output signal 116 from NAND gate 113 which is high is inverted by inverter 152 and is supplied as an enabling signal to the four-line-to-sixteen-line decoder/demultiplexer 171. When pins 18 and 19 of the four-line-to-sixteen-line decoder/demultiplexer 171 are low the four-line-to-sixteen-line decoder/demultiplexer 171 is enabled to accept signals 154–157 from the synchronous four-bit binary counter 151. Signals 154–157 will represent a binary number. The four-line-to-sixteen-line decoder/demultiplexer 171 will switch to low the particular output signal 175–190 corresponding to the address contained in the binary combination of signals 154–157. The first address available will be 0000. The output signal 175 from the four-line-to-sixteen-line decoder/demultiplexer 171 will be switched low in response to this address. This process will continue until the synchronous four bit binary counter 151 reaches a count of 15. The output signal 190 from the four line to sixteen line decoder/demultiplexer 171 will be switched low in response to a count signal of 15. The output signals 175-190 from the four-line-to-sixteen-line decoder/demultiplexer are inverted by inverters 191-206 to form the output signals 207-222 from the sequencing circuit 62 which will be high. In a preferred embodiment, control signal 64, shown in FIG. 1 from the sequencing circuit 62, corresponds to signal 207 shown in FIG. 4. The control signal 63, from the sequencing circuit 62, corresponds to signal 208. Control signal 65, from the sequencing circuit 62, corresponds to signal 209. Control signal 66, from the sequencing circuit 62, corresponds to signal 210.

When the synchronous four-bit binary counter 151 reaches a count of 15, signal 153 will go high. Signal 153 is inverted by inverter 115 and is supplied as an input to pin 13 of NAND gate 114. The output signal 116 from NAND gate 113 will then go low which will stop the pulses from the four-input buffer 131 and which will also drive pins 18 and 19 of the four-line-to-sixteen-line decoder/demultiplexer 171 high, thus not allowing any output from the four-line-to-sixteen-line decoder/demultiplexer 171 to go low.

The above described cycle is repeated when control signal 61 triggers the sequencing circuit again, at the beginning of another chromatographic analyzer cycle period.

The invention has been described in terms of its presently preferred embodiment as is shown in FIGS. 1 and 4. For the sake of convenience, many of the signals which supply power to the various chips shown in the schematic of FIGS. 1 and 4 have been omitted. Voltage levels required by various chips are specified by the manufacturers and are well known to those familiar with the art.

Many different circuit configurations are possible which would perform the functions required of the circuits shown in FIGS. 1 and 2. These figures are illustrative of particular circuit configurations which will perform the required functions.

Specific components which are available commercially and which can be used in the practice of the invention as shown in FIGS. 1 and 2 follow. Values of resistors and capacitors used in these particular circuits are also given. Again, many different combinations of circuit values particularly in the area of resistance and capacitance values are possible.

| Resistors | | TRS/IRC |
|---|---|---|
| 22,27,28,43,48,58,92,93,98, | 10 KΩ | RN55D |
| 25,83 | 4.99 KΩ | RN55D |
| 46,96 | 3.32 KΩ | RN55D |
| 72 | 1.82 KΩ | RN55D |
| 76 | 15 KΩ | RN55D |
| 81,86 | 8.25 KΩ | RN55D |
| Potentiometers 52,56 | 10K | Bourns 3500-103 |
| Capacitors 15,35,77 | .01 µf | Sprague 7CZ5U103X0050D1 |
| Capacitor 85 | .002 µf | Sprague 5GA-D20 |
| Operational Amplifiers 16,33 | | 3523L, Burr-Brown |
| Operational Amplifiers 24,44,53, 57,95 | | MA 741C, Fairchild Smeiconductors |
| Operational Amplifier 73 | | 3542J, Burr-Brown |
| Operational Amplifier 82 | | 558, Signetics |
| Switching means 14,32,42,88 | | Quad Bilateral Switch CD4016C National Semiconductor |
| Inverters 112,115,141,152,191-206 | | Hex Inverters DM937 National Semiconductor |
| 2-Input Buffer 111 | | Quad 2-input buffer DM957 National Semiconductor |
| Synchronous 4-Bit Binary Counter 151 | | DM9316, National Semiconductor |
| 4-Input Buffer 131 | | DM932, National Semiconductor |
| 4-Line to 16-Line Decoders/Demultiplexers 171 | | Dm9311, National Semiconductor |

While the invention has been described in terms of the presently preferred embodiment, reasonable variations and modifications are possible by those skilled in the art, within the scope of the described invention and the appended claims.

That which is claimed is:

1. Apparatus comprising:
   means for establishing a first signal which is continuous in time;
   first sampling means for sampling said first signal and for establishing a second signal representative of the sampled value of said first signal at a point in time $t_1$;
   second sampling means for sampling said first signal and for establishing a third signal representative of the sampled value of said first signal at a point in time $t_2$ which is later in time than said point in time $t_1$;
   means for combining said second signal and said third signal to produce a fourth signal representative of said second signal subtracted from said third signal;
   means for dividing said fourth signal by the sample period T, where T is defined as said point in time $t_1$ subtracted from said point in time $t_2$, to establish a fifth signal;
   means for integrating said fifth signal over said sample period T to establish a sixth signal; and
   means for combining said third signal and said sixth signal to establish a seventh signal representative of a prediction of the value of said first signal at points in time between said point in time $t_2$ and a point in time $t_3$ which is later in time than said point in time $t_2$.

2. Apparatus in accordance with claim 1 wherein said means for establishing said fourth signal comprises:
   inverting means for accepting said third signal and for establishing an eighth signal representative of the inversion of said third signal; and
   summing amplifier means for combining and inverting said eighth signal and said second signal to establish said fourth signal.

3. A method for implementing a first order sample and hold comprising the steps of:
   establishing a first signal which is continuous in time;
   sampling said first signal and establishing a second signal representative of the sampled value of said first signal at a point in time $t_1$;
   sampling said first signal and establishing a third signal representative of the sampled value of said first signal at a point in time $t_2$ which is later in time than said point in time $t_1$;
   combining said second signal and said third signal to produce a fourth signal representative of said second signal subtracted from said third signal;
   dividing said fourth signal by the sample period T, where T is defined as said point in time $t_1$ subtracted from said point in time $t_2$, to establish a fifth signal;
   integrating said fifth signal over said sample period T to establish a sixth signal; and
   combining said third signal and said sixth signal to establish a seventh signal representative of a prediction of the value of said first signal at points in time between said point in time $t_2$ and a point in time $t_3$ which is later in time than said point in time $t_2$.

4. A method in accordance with claim 3 wherein said step of establishing said fourth signal comprises inverting and combining said fifth signal and said second signal to establish said fourth signal.

* * * * *